United States Patent [19]

Lesher et al.

[11] Patent Number: 4,504,482
[45] Date of Patent: Mar. 12, 1985

[54] [5(OR 4)-(PYRIDINYL)-2-PYRIMIDINYL]UREAS AND CARDIOTONIC USE THEREOF

[75] Inventors: George Y. Lesher, Schodack; Baldev Singh, East Greenbush, both of N.Y.

[73] Assignee: Sterling Drug Inc., New York, N.Y.

[21] Appl. No.: 518,280

[22] Filed: Jul. 28, 1983

[51] Int. Cl.$^3$ .................. A61K 31/505; C07D 401/04
[52] U.S. Cl. ..................................... 514/275; 544/331
[58] Field of Search ......................... 544/331; 424/251

[56] References Cited
U.S. PATENT DOCUMENTS 4,008,235  2/1977  Lesher et al. ..................... 424/251

OTHER PUBLICATIONS

Lesher, Singh and Mielens, [J. Med. Chem., 25(7), 837–842, (1982)].
Bennett et al., Journal of Medicinal Chemistry, 1978, vol. 21, No. 7, pp. 623–627.

Primary Examiner—Donald G. Daus
Assistant Examiner—Cecilia Shen
Attorney, Agent, or Firm—Robert K. Bair; B. Woodrow Wyatt; Paul E. Dupont

[57] ABSTRACT

N-R-N'-R'-N-[4(or 5)-PY-2-pyrimidinyl]ureas (I) or salts thereof, where PY is 4- or 3-pyridinyl or 4- or 3-pyridinyl having one or two lower-alkyl substituents, R' is hydrogen or methyl and R is methyl or ethyl when PY is attached to the 4-position of the pyrimidine ring or R is hydrogen, ethyl or n-butyl when PY is attached to the 5-position of the pyrimidine ring are useful as cardiotonic agents. The preparations of I and their cardiotonic use are shown.

8 Claims, No Drawings

[5(OR 4)-(PYRIDINYL)-2-PYRIMIDINYL]UREAS AND CARDIOTONIC USE THEREOF

CROSS-REFERENCE TO RELATED APPLICATION

4(or 5)-(pyridinyl)-2-pyrimidinamines, some of which are used as intermediates herein, and their cardiotonic use are disclosed and claimed in copending application Ser. No. 516,820, filed July 25, 1983.

BACKGROUND OF THE INVENTION (a) Field of the Invention

This invention relates to [5(or 4)-(pyridinyl)-2-pyrimidinyl]ureas and their cardiotonic use.

(b) Information Disclosure Statement

N-[4-(4-pyridinyl)-2-pyrimidinyl]urea (no. 4k) was reported by Bennett et al. [J. Med. Chem. 21(7), 623–8 (1978)] as producing a reduction in paw volume of 12% at 100 mg/kg in the carrageenan foot edema test in the rat. Compound no. 4k was prepared by hydrolysis of the corresponding N-cyano-4-(4-pyridinyl)-2-pyrimidinamine (4f). Other compounds disclosed include, inter alia, 4-(4-pyridinyl)-2-pyrimidinamine (4a), 4-(3-pyridinyl)-2-pyrimidinamine (4e) and N-methyl-4-(4-pyridinyl)-2-pyrimidinamine (4g), Discussion in the Bennett et al reference regarding the antiinflammatory activity of the compounds disclosed therein concluded as follows:

"None of the compounds tested against adjuvant-induced edema in the rat displayed a level of activity sufficient to warrant further investigation. Based on additional testing it would appear that these compounds represent a series of false positives in the carrageenan-induced edema model."

Isomeric N—R—N'—[2-(4-,3- or 2-pyridinyl)-4-pyrimidinyl]ureas, useful as allergy inhibitors, are disclosed and claimed in Lesher and Singh U.S. Pat. No. 4,008,235, issued Feb. 15, 1977, and in a Lesher, Singh and Mielens publication [J. Med. Chem. 25(7), 837–842 (1982)].

SUMMARY OF THE INVENTION

In a composition of matter aspect, the invention resides in N—R—N'—R'—N'—[4(or 5)-PY-2-pyrimidinyl]urea having the formula I

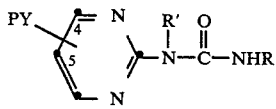

or acid-addition salt thereof, where PY is 4- or 3-pyridinyl or 4- or 3-pyridinyl having one or two lower-alkyl substituents, R' is hydrogen or methyl and R is methyl or ethyl when PY is attached to the 4-position of the pyrimidine ring or R is hydrogen, ethyl or n-butyl when PY is attached to the 5-position of the pyrimidine ring. The compounds of formula I are useful as cardiotonic agents, as determined by standard pharmacological evaluation procedures.

A composition aspect of the invention resides in the cardiotonic composition for increasing cardiac contractility, said composition comprising a pharmaceutically acceptable inert carrier and, as the active component thereof, a cardiotonically effective amount of N—R—N'—R'—N'—[4(or 5)-PY-2-pyrimidinyl]urea having formula I, where PY, R' and R are defined as in formula I, or pharmaceutically acceptable acid-addition salt thereof.

In a method aspect, the invention resides in the method for increasing cardiac contractility in a patient requiring such treatment which comprises administering orally or parenterally in a solid or liquid dosage form to such patient a cardiotonically effective amount of N—R—N'—R'—N'—[4(or 5)-PY-2-pyrimidinyl]urea having formula I, where PY, R' and R are defined as in formula I, or pharmaceutically acceptable acid-addition salt thereof.

DETAILED DESCRIPTION INCLUSIVE OF PREFERRED EMBODIMENTS

Preferred embodiments are those of formula I where PY is 4-pyridinyl or 3-pyridinyl, R' is hydrogen and R is ethyl when PY is attached to the 4-position of the pyrimidine ring and R is hydrogen or n-butyl when PY is attached to the 5-position of the pyrimidine ring.

The term "lower-alkyl" as used herein, e.g., as a substituent for PY, means alkyl radicals having from one to four carbon atoms which can be arranged as straight or branched chains, illustrated by methyl, ethyl, n-propyl, isopropyl, n-butyl, 2-butyl and isobutyl.

The symbol "PY" as used herein, e.g., as the 4- or 5-substituent in the pyrimidine ring of the compounds having formula I, means 4- or 3-pyridinyl or 4- or 3-pyridinyl having one or two lower-alkyl substituents, illustrated by 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2,6-diethyl-4-pyridinyl, 2,6-diethyl-3-pyridinyl, 2,6-diisopropyl-4-pyridinyl, and the like.

The compounds of the invention having formula I are useful both in the free base form and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base of the cardiotonically active compounds of the invention are not vitiated by side effects ascribable to the anions. In practicing the invention, it is convenient to use the free base form; however, appropriate pharmaceutically acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, which give the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds of the invention were assigned on the basis of evidence provided by infrared, nuclear magnetic resonance and mass spectra, by the correspondence of calculated and found values for the elementary analyses, and, by their method of preparation.

The manner of making and using the instant invention will now be generally described so as to enable a person skilled in the art of pharmaceutical chemistry to make and use the same, as follows.

The compounds of formula I where R is methyl, ethyl or n-butyl are prepared by reacting N—R'-4(or 5)-PY-2-pyrimidinamine, where R' and PY are defined as in formula I, with methyl, ethyl or n-butyl isocyanate. This reaction is conveniently carried out by mixing said reactants, preferably in a molar ratio of 1:1 with stirring at about 20° to 150° C., preferably about 20° to 60° C., preferably using a suitable inert solvent and using the said N—R'-4(or 5)-PY-2-pyrimidinamine as its alkali metal salt, preferably the sodium salt which is conveniently prepared using sodium hydride dispersed in mineral oil. Preferred solvents are aprotic solvents, especially dimethyl sulfoxide and dimethylformamide. Other inert aprotic solvents which can be used include dimethylthiourea, tetramethylurea, dimethylacetamide, hexamethylphosphoramide, N-methylpyrrolidine, and the like. The reaction also can be run by heating N—R'-4(or 5)-PY-2-pyrimidinamine in free base form with methyl, ethyl or n-butyl isocyanate at about 100°–200° C. in the absence of a solvent or in an inert solvent, e.g., said aprotic solvents and also toluene, xylene, chlorobenzene, anisole, and the like; however, the reaction takes longer.

The intermediate N—R'-4-PY-2-pyrimidinamines are generally known and are prepared by known means as described by Bennett et al., [J. Med. Chem. 21(7), 623–8 (1978)].

The intermediate N—R'-5-PY-2-pyrimidinamines, which are disclosed and claimed in copending application Ser. No. 516,820, filed July 25, 1983, were prepared by heating guanidine or an acid-addition salt thereof, e.g., sulfate or carbonate, with 3-dimethylamino-2-PY-2-propen-1-al. When the guanidine salt is derived from a strong acid, e.g., sulfuric or hydrochloric acid, the reaction is run in the presence of a base such as an alkali lower-alkoxide in a lower-alkanol, preferably sodium ethoxide or methoxide in refluxing ethanol or methanol. Although base can be used, it is unnecessary when using a guanidine salt of a weak acid, such as a carbonate or an acetate. Other solvents can be used, for example, n-propanol, 2-propanol, p-dioxane, tetrahydrofuran, dimethylformamide, 1,2-dimethoxyethane, and the like.

The N-[5-PY-2-pyrimidinyl]ureas of formula I where R and R' are each hydrogen are conveniently prepared in two steps by first heating a mixture containing 3-dimethylamino-2-PY-2-propenal, dicyandiamide, in alkali lower-alkoxide and a lower-alkanol, preferably sodium methoxide or ethoxide and methanol or ethanol, to produce N-cyano-5-PY-2-pyrimidinamine and partially hydrolyzing said N-cyano compound by heating it with aqueous mineral acid, e.g., 6N sulfuric acid, to produce said N-[5-PY-2-pyrimidinyl]urea of formula I where R and R' are each hydrogen and PY is defined as in formula I.

The following examples will further illustrate the invention without, however, limiting it thereto.

A. 4(or 5)-PY-2-PYRIMIDINAMINES

A-1. 5-(4-Pyridinyl)-2-pyrimidinamine—A mixture containing 20 g of 3-dimethylamino-2-(4-pyridinyl)-2-propen-1-al, 25 g of guanidine carbonate and 100 ml of ethanol was refluxed for 4 hours and concentrated in vacuo to remove the solvent. The residue was stirred in ice cold water and the crystalline product was collected, washed with water and dried to produce 12.1 g of 5-(4-pyridinyl)-2-pyrimidinamine, m.p. 210°–212° C.

A-2. N-Methyl-5-(4-pyridinyl)-2-pyrimidinamine, m.p. 180°–182° C., 8.7 g, was prepared following the procedure described in Example A-1 using 17.6 g of 3-dimethylamino-2-(4-pyridinyl)-2-propen-1-al, 24.4 g of 1-methylguanidine sulfate, 10.8 g of sodium methoxide and 100 ml of ethanol.

Following the procedure of Example A-1 using in place of 3-dimethylamino-3-methyl-2-(4-pyridinyl)-2-propen-1-al and guanidine carbonate molar equivalent quantities of the appropriate 3-dimethylamino-2-PY-2-propen-1-al and guanidine derivative, it is contemplated that the corresponding N—R'-5-PY-2-pyrimidinamines of Examples A-3 through A-6 can be obtained.

A-3. 5-(3-Pyridinyl)-2-pyrimidinamine, using 3-dimethylamino-2-(3-pyridinyl)-2-propen-1-al and guanidine carbonate.

A-4. 5-(2-Methyl-3-pyridinyl)-2-pyrimidinamine, using 3-dimethylamino-2-(2-methyl-3-pyridinyl)-2-propen-1-al and guanidine carbonate.

A-5. 5-(2-Methyl-4-pyridinyl)-2-pyrimidinamine, using 3-dimethylamino-2-(2-methyl-4-pyridinyl)-2-propen-1-al and guanidine sulfate.

A-6. N-Methyl-5-(2,6-dimethyl-4-pyrindinyl)-2-pyrimidinamine, using 3-dimethylamino-2-(2,6-dimethyl-4-pyridinyl)-2-propen-1-al and 1-methylguanidine sulfate.

Following the procedure described by Bennett et al., supra, but using in place of 3-dimethylamino-1-(4-pyridinyl)-2-propen-1-one, and guanidine or 1-methylguanidine [whereby 4-pyridinyl)-2-pyrimidinamine and N-methyl-4-(4-pyridinyl)-2-pyrimidinamine were obtained] molar equivalent quantities of the appropriate 3-dimethylamino-1-PY-2-propen-1-one and guanidine derivative, it is contemplated that the corresponding N—R'-4-PY-2-pyrimidinamines of Examples A-7 through A-10 can be obtained.

A-7. 4-(2-Methyl-3-pyridinyl)-2-pyrimidinamine, using 3-dimethylamino-1-(2-methyl-3-pyridinyl)-2-propen-1-one and guanidine.

A-8. 4-(2-Methyl-4-pyridinyl)-2-pyrimidinamine, using 3-dimethylamino-1-(2-methyl-4-pyridinyl)-2-propen-1-one and guanidine.

A-9. 4-(2,6-Dimethyl-4-pyridinyl)-2-pyrimidinamine, using 3-dimethylamino-1-(2,6-dimethyl-4-pyridinyl)-2-propen-1-one and guanidine.

A-10. N-Methyl-4-(3-pyridinyl)-2-pyrimidinamine, using 3-dimethylamino-1-(3-pyridinyl)-2-propen-1-one and 1-methylguanidine.

B. N-[4(or 5)-PY-2-PYRIMIDINYL]UREAS

B-1. N-Ethyl-N'-[4-(4-pyridinyl)-2-pyrimidinyl]urea—To a solution containing 12.1 g of 4-(4-pyridinyl)-2-pyrimidinamine dissolved in 200 ml of dimethylformamide was added 3.4 g of sodium hydride and the resulting mixture was stirred at room temperature until there was no further evoltuion of hydrogen. To the stirred mixture was added 6.0 g of ethyl isocyanate and the resulting mixture was stirred at room temperature overnight. The reaction mixture was poured into water and the separated solid was collected, washed with n-hexane and then dissolved in 700 ml of methanol. The methanol solution was treated with decolorizing charcoal and filtered; and, to the filtrate was added 300 ml of n-hexane. All but about 250 ml of the combined solvent was removed on a rotary evaporator and the mixture cooled. The solid product was collected, washed with n-hexane and dried to yield 12.7 g of N-ethyl-N'-[4-(4-pyridinyl)-2-pyrimidinyl]urea, m.p. 204°–207° C.

Acid-addition salts of N-ethyl-N'-[4-(4-pyridinyl)-2-pyrimidinyl]urea are conveniently prepared by adding to a mixture of 1 g N-ethyl-N'-[4-(4-pyridinyl)-2-pyrimidinyl]urea in about 20 ml of aqueous methanol the appropriate acid, e.g, methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of N-ethyl-N'-[4-(4-pyridinyl)-2-pyrimidinyl]urea and the appropriate acid, e.g., lactic acid or hydrochloric acid, to prepare respectively the lactate or hydrochloride salt of N-ethyl-N'-[4-(4-pyridinyl)-2-pyrimidinyl]urea in aqueous solution.

B-2. N-Methyl-N'-[4-(4-pyridinyl)-2-pyrimidinyl]urea, m.p. 215°–218° C., 5.7 g, was prepared following the procedure described in Example B-1 using 12.1 g of 4-(4-pyridinyl)-2-pyrimidinamine, 150 ml of dimethylformamide, 3.5 g of sodium hydride and 5 g of methyl isocyanate.

B-3. N-Ethyl-N'-[5-(4-pyridinyl)-2-pyrimidinyl]urea—To a mixture containing 12.9 g of 5-(4-pyridinyl)-2-pyrimidinmaine and 4.0 g of sodium hydride (50% in mineral oil) chilled in an ice bath was added dropwise with stirring a solution containing 7.1 ml of ethyl isocyanate dissolved in 45 ml of dimethylformamide. The reaction mixture was stirred at room temperature for about 3 hours and then excess water was added. The mixture was acidified with acetic acid and cooled. The separated product was collected, recrystallized from ethanol and dried in vacuo at 60° C. to produce 10.5 g of N-ethyl-N'-[5-(4-pyridinyl)-2-pyrimidinyl]urea, m.p. 241°–246° C.

Acid-addition salts of N-ethyl-N'-[5-(4-pyridinyl)-2-pyrimidinyl]urea prepared by adding to a mixture of 1 g of N-ethyl-N'-[5-(4-pyridinyl)-2-pyrimidinyl]urea in about 20 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of N-ethyl-N'-[5-(4-pyridinyl)-2-pyrimidinyl]urea and the appropriate acid, e.g., lactic acid or hydrochloric acid, to prepare respectively the lactate or hydrochloride salt of N-ethyl-N'-[5-(4-pyridinyl)-2-pyrimidinyl]urea in aqueous solution.

B-4. N-n-Butyl-N'-methyl-N'-[5-(4-pyridinyl)-2-pyrimidinyl]urea—A mixture containing 12.3 g of N-methyl-5-(4-pyridinyl)-2-pyrimidinamine and 50 ml of n-butyl isocyanate was refluxed for about 8 hours and then cooled. The reaction mixture was slurried with ether. The product was collected, recrystallized from n-hexane-ethyl acetate and dried in vacuo at 50° C. to produce 12.5 g of N-n-butyl-N'-methyl-N'-[5-(4-pyridinyl)-2-pyrimidinyl]urea, m.p. 97°–99° C.

B-5. N-n-Butyl-N'-[5-(4-pyridinyl)-2-pyrimidinyl]urea—To a mixture containing 5.0 g of 50% sodium hydride dispersed in mineral oil and 200 ml of dimethyl sulfoxide was added 17 g of 5-(4-pyridinyl)-2-pyrimidinamine and the mixture was stirred at room temperature until the evolution of hydrogen ceased. To this stirred mixture at room temperature was added dropwise 9.9 g of n-butyl isocyanate in 25 ml of dimethyl sulfoxide. The reaction mixture was then stirred for about 1 hour and poured into a mixture of ice and water. The mixture was stirred until the product was filterable. The product was collected, washed successively with water and acetonitrile, dried, recrystallized from methanol, washed with ether and dried to yield 17.5 g of N-n-butyl-N'-[5-(4-pyridinyl)-2-pyrimidinyl]urea, m.p. 204°–206° C.

B-6. N-[5-(4-Pyridinyl)-2-pyrimidinyl]urea—A mixture containing 9.0 g of N-cyano-5-(4-pyridinyl)-2-pyrimidinamine and 200 ml of 6N sulfuric acid was heated to near reflux for 20 minutes, cooled and then poured slowly into a mixture containing 1200 ml of 2N aqueous sodium hydroxide solution and 200 g of ice. The pH of this mixture was brought to about 9–10 using excess 2N sodium hydroxide solution. The alkaline solution was cooled and the separated product was collected, recrystallized from dimethylformamide, dried in vacuo at 110° C. to yield 4.5 g of N-[5-(4-pyridinyl)-2-pyrimidinyl]urea, m.p. >250° C.

Acid-addition salts of N-[5-(4-pyridinyl)-2-pyrimidinyl]urea are conveniently prepared by adding to a mixture of 1 g of N-[5-(4-pyridinyl)-2-pyrimidinyl]urea in about 20 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of N-[5-(4-pyridinyl)-2-pyrimidinyl]urea and the appropriate acid, e.g., lactic acid or hydrochloric acid, to prepare respectively the lactate or hydrochloride salt of N-[5-(4-pyridinyl)-2-pyrimidinyl]urea in aqueous solution.

The above intermediate N-cyano-5-(4-pyridinyl)-2-pyrimidinamine, alternatively named [5-(4-pyridinyl)-2-pyrimidinyl]cyanamide, was prepared as follows: A mixture containing 19.4 g of 3-dimethylamino-2-(4-pyridinyl)-2-propen-1-al, 8.4 g of dicyandiamide, 10.8 g of sodium methoxide and 200 ml of methanol was refluxed for 30 minutes and cooled. The solid was collected, dried, dissolved in water and the aqueous solution neutralized with acetic acid. The solid was collected, washed with water, dried, recrystallized from dimethylformamide, washed successively with ethanol and ether, and dried to yield 9.5 g of N-cyano-5-(4-pyridinyl)-2-pyrimidinamine, m.p. >300° C.

Following the procedure described in the immediately preceding paragraph for preparing N-cyano-5-(4-pyridinyl)-2-pyrimidinamine but using in place of 3-dimethylamino-2-(4-pyridinyl)-2-propen-1-al a molar equivalent quantity of the corresponding 3-dimethylamino-2-PY-2-propen-1-al, it is contemplated that the following N-cyano-5-PY-2-pyrimidinamines can be obtained: N-cyano-5-(3-pyridinyl)-2-pyrimidinamine using 3-dimethylamino-2-(3-pyridinyl)-2-propen-1-al; N-cyano-5-(2-methyl-4-pyridinyl)-2-pyrimidinamine using 3-dimethylamino-2-(2-methyl-4-pyridinyl)-2-propen-1-al; and N-cyano-5-(2,6-dimethyl-4-pyridinyl)-2-pyrimidinamine using 3-dimethylamino-2-(2,6-dimethyl-4-pyridinyl)-2-propen-1-al.

Following the procedure described in Example B-1 but using in place of 4-(4-pyridinyl)-2-pyrimidinamine and ethyl isocyanate corresponding molar equivalent quantities of the appropriate N—R'-4(or 5)-PY-2-pyrimidinamines and ethyl or n-butyl isocyanate, it is contemplated that the following N-(ethyl or n-butyl)-N'—R'—N'-[4(or 5)-PY-2-pyrimidinyl]ureas of Examples B-7 through B-15 can be obtained.

B-7. N-Ethyl-N'-methyl-N'-[4-(3-pyridinyl)-2-pyrimidinyl]urea, using N-methyl-4-(3-pyridinyl)-2-pyrimidinamine and ethyl isocyanate.

B-8. N-Ethyl-N'-[5-(3-pyridinyl)-2-pyrimidinyl]urea, using 5-(3-pyridinyl)-2-pyrimidinamine and ethyl isocyanate.

B-9. N-n-Butyl-N'-[5-(3-pyridinyl)-2pyrimidinyl]urea, using 5-(3-pyridinyl)-2-pyrimidinamine and n-butyl isocyanate.

B-10. N-Ethyl-N'-[5-(2-methyl-3-pyridinyl)-2-pyrimidinyl]urea, using 5-(2-methyl-3-pyridinyl)-2-pyrimidinamine and ethyl isocyanate.

B-11. N-n-Butyl-N'-[5-(2-methyl-4-pyridinyl)-2-pyrimidinyl]urea, using 5-(2-methyl-4-pyridinyl)-2-pyrimidinamine and n-butyl isocyanate.

B-12. N-Ethyl-N'-5-[2,6-dimethyl-4-pyridinyl)-2-pyrimidinyl]urea, using 5-(2,6-dimethyl-4-pyridinyl)-2-pyrimidinamine and ethyl isocyanate.

B-13. N-Ethyl-N'-[4-(2-methyl-3-pyridinyl)-2-pyrimidinyl]urea, using 4-(2-methyl-3-pyridinyl)-2-pyrimidinamine and ethyl isocyanate.

B-14. N-n-Butyl-N'-[4-(2-methyl-4-pyridinyl)-2-pyrimidinyl]urea, using 4-(2-methyl-4-pyridinyl)-2-pyrimidinamine and n-butyl isocyanate.

B-15. N-Ethyl-N'-[4-(2,6-dimethyl-4-pyridinyl)-2-pyrimidinyl]urea, using 4-(2,6-dimethyl-4-pyridinyl)-2-pyrimidinamine and ethyl isocyanate.

Following the procedure described in Example B-6 but using in place of N-cyano-5-(4-pyridinyl)-2-pyrimidinamine a molar equivalent quantity of the corresponding N-cyano-5-PY-2-pyrimidinamine, it is contemplated that the following N-(5-PY-2-pyrimidinyl-)ureas of Examples B-16 through B-18 can be obtained.

B-16. N-[5-(3-Pyridinyl)-2-pyrimidinyl]urea, using N-cyano-5-(3-pyridinyl)-2-pyrimidinamine.

B-17. N-[5-(2-Methyl-4-pyridinyl)-2-pyrimidinyl]urea, using N-cyano-5-(2-methyl-4-pyridinyl)-2-pyrimidinamine.

B-18. N-[5-(2,6-Dimethyl-4-pyridinyl)-2-pyrimidinyl]urea, using N-cyano-5-(2,6-dimethyl-4-pyridinyl)-2-pyrimidinamine.

The usefulness of the compounds of formula I or pharmaceutically acceptable acid-addition salts thereof as cardiotonic agents is demonstrated by their effectiveness in standard pharmacological test procedures, for example, in causing a significant increase in the contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1978.

When tested by the isolated cat or guinea pig atria and papillary muscle procedure, the compounds of formula I or pharmaceutically acceptable acid-addition salts thereof at doses of 10, 30 and/or 100 μg/ml, were found to cause significant increases, that is, greater than 25% (cat) or 30% (guinea pig) in papillary muscle force and significant increases, that is, greater than 25% (cat) or 30% (guinea pig), in right atrial force, while causing a lower percentage increase in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, when tested at one or more of said dose levels by this procedure in the cat or guinea pig test, the compounds of the invention were found to cause respective increases in papillary muscle force (PMF) and right atrial force (RAF) given in Table A.

TABLE A

| | | | In Vitro Cardiotonic Activity | | | |
|---|---|---|---|---|---|---|
| | Cat | Dose | Percentage Increase | | | |
| Example | or g.p. | μg/ml | RAR[a] | RAF[b] | PMF[c] | N[d] |
| B-1 | g.p. | 30 | 14 | 90 | 104 | 1/5 |
| | | 100 | 34 | 255 | 199 | 1/5 |
| B-2 | g.p. | 30 | 13 | 34 | 35 | 1/5 |
| | | 100 | 17 | 33 | 39 | 1/5 |
| B-3 | g.p. | 100 | 25 | 162 | 107 | 1/5 |
| B-4 | g.p. | 10 | 20 | 60 | 65 | 1/5 |
| | | 30 | 34 | 81 | 109 | 1/5 |
| | | 100 | 25 | 76 | 98 | 1/5 |
| B-5 | cat | 10 | 11 | 26 | 39 | 1/7 |
| B-6 | g.p. | 10 | 13 | 39 | 54 | 1/9 |
| | | 30 | 18 | 123 | 108 | 1/8 |
| | | 100 | 25 | 297 | 198 | 1/8 |

[a]Right atrial rate.
[b]Right atrial force.
[c]Papillary muscle force.
[d]Number of preparations.

When tested by said anesthetized dog procedure, the compounds of formula I at doses of 1.0, 3.0 and/or 10.0 mg/kg administered intravenously were found to cause significant increases, that is, 25% or greater, in cardiac contractile force or cardiac contractility with lower changes in heart rate and blood pressure. For example, when tested at one or more of said dose levels by this procedure, the compounds of Examples B-5 and B-6 were found to cause increases of about 35% to 126% in contractile force and lower changes in heart rate and blood pressure.

The present invention includes within its scope a cardiotonic composition comprising a pharmaceutically acceptable carrier and, as the active component thereof, the cardiotonic compound of formula I or pharmaceutically acceptable acid-addition salt thereof. The invention also includes within its scope the method for increasing cardiac contractility in a patient requiring such treatment which comprises administering to such patient a cardiotonically effective amount of the compound of formula I or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc, and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic ester such as ethyl oleate. These compositions can also contain adjuvants such as stabilizing, preserving, wetting, emulsifying and dispersing agents.

They can be sterilized, for example by filtration through a bacterial-retaining filter, by incorporation of sterilizing agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied to that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. An N—R—N'—R'—N'—[4-(or 5)-PY-2-pyrimidinyl]urea having the formula

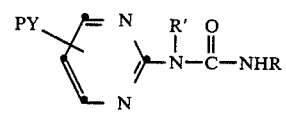

or acid-addition salt thereof, where PY is 4- or 3-pyridinyl or 4- or 3-pyridinyl having one or two lower-alkyl substituents, R' is hydrogen or methyl and R is methyl or ethyl when PY is attached to the 4-position of the pyrimidine ring or R is hydrogen, ethyl or n-butyl when PY is attached to the 5-position of the pyrimidine ring.

2. An N—R—N'—R'—N'—(4-PY-2-pyrimidinyl)urea according to claim 1 where PY is 4-pyridinyl or 3-pyridinyl, R' is hydrogen and R is ethyl.

3. An N—R—N'—R'—N'—(5-PY-2-pyrimidinyl)urea according to claim 1 where PY is 4-pyridinyl or 3-pyridinyl, R' is hydrogen and R is hydrogen or n-butyl.

4. N-Ethyl-N'-[4-(4-pyridinyl)-2-pyrimidinyl]urea according to claim 1.

5. N-n-Butyl-N'-[5-(4-pyridinyl)-2-pyrimidinyl]urea according to claim 1.

6. N-[5-Pyridinyl)-2-pyrimidinyl]urea according to claim 1.

7. A cardiotonic composition for increasing cardiac contractility, said composition comprising a pharmaceutically acceptable inert carrier and, as the active component thereof, a cardiotonically effective amount of N—R—N'—R'—N'—[4(or 5)-PY-2-pyrimidin]urea according to claim 1 or pharmaceutically acceptable acid-addition salt thereof.

8. The method for increasing cardiac contractility in a patient requiring such treatment which comprises administering orally or parenterally in a solid or liquid dosage form to such patient a cardiotonically effective amount of N—R—N'—R'—N'—[4(or 5)-PY-2-pyrimidinyl]urea according to claim 1 or pharmaceutically acceptable acid-addition salt thereof.

* * * * *

UNITED STATES PATENT AND TRADEMARK OFFICE
CERTIFICATE OF CORRECTION

PATENT NO. : 4,504,482

DATED : March 12, 1985

INVENTOR(S) : George Y. Lesher & Baldev Singh

It is certified that error appears in the above-identified patent and that said Letters Patent is hereby corrected as shown below:

Column 10, Claim 6, line 34, "N-[5-Pyridinyl)" should read -- N-[5-(4-Pyridinyl) --.

Signed and Sealed this

Nineteenth Day of November 1985

[SEAL]

Attest:

Attesting Officer

DONALD J. QUIGG

Commissioner of Patents and Trademarks